United States Patent
McFarlin et al.

[11] Patent Number: 5,667,478
[45] Date of Patent: Sep. 16, 1997

[54] SURGICAL INSTRUMENT WITH STICK-ON FIBER-OPTIC VIEWING SYSTEM AND METHOD OF USING

[75] Inventors: Whitney A. McFarlin, Minneapolis; Thomas C. Barthel, Becker; Miles A. Finn, Minneapolis, all of Minn.

[73] Assignee: Clarus Medical Systems, Inc., Minneapolis, Minn.

[21] Appl. No.: 428,258

[22] PCT Filed: Nov. 6, 1992

[86] PCT No.: PCT/US92/09564

§ 371 Date: May 3, 1995

§ 102(e) Date: May 3, 1995

[87] PCT Pub. No.: WO94/11771

PCT Pub. Date: May 26, 1994

[51] Int. Cl.⁶ .................................. A61B 1/005
[52] U.S. Cl. .................. 600/182; 600/101; 600/160; 385/117
[58] Field of Search ..................... 600/182, 160, 600/188, 199; 385/114–117, 53, 133, 135, 136; 362/32; 206/438, 439

[56] References Cited

U.S. PATENT DOCUMENTS

| | | |
|---|---|---|
| 2,068,721 | 1/1937 | Wappler et al. . |
| 2,691,370 | 10/1954 | Wallace . |
| 3,664,330 | 5/1972 | Deutsch . |
| 3,758,951 | 9/1973 | Scrivo et al. ........................... 433/29 |
| 3,882,854 | 5/1975 | Huylka et al. . |
| 4,300,564 | 11/1981 | Furihata . |
| 4,471,766 | 9/1984 | Terayama . |
| 4,588,294 | 5/1986 | Siegmund . |
| 4,597,030 | 6/1986 | Brody et al. ...................... 385/114 X |
| 4,616,631 | 10/1986 | Takahashi . |
| 4,620,547 | 11/1986 | Boebel . |
| 4,651,201 | 3/1987 | Schoolman . |
| 4,656,999 | 4/1987 | Storz . |
| 4,759,348 | 7/1988 | Cawood . |
| 4,782,819 | 11/1988 | Adair . |
| 4,867,529 | 9/1989 | Utsumi et al. . |
| 4,911,525 | 3/1990 | Hicks et al. ............................. 385/114 |
| 5,016,098 | 5/1991 | Cooper et al. . |
| 5,147,356 | 9/1992 | Bhatta . |
| 5,178,267 | 1/1993 | Grabenkort et al. .................. 206/439 |
| 5,230,621 | 7/1993 | Jacoby . |
| 5,246,109 | 9/1993 | Markle et al. ....................... 206/439 |
| 5,281,134 | 1/1994 | Schultz . |
| 5,312,400 | 5/1994 | Bales et al. . |
| 5,373,840 | 12/1994 | Knighton . |
| 5,535,105 | 7/1996 | Myerskoenen et al. ............... 362/32 |

FOREIGN PATENT DOCUMENTS

| | | |
|---|---|---|
| 0 316 816 | 5/1989 | European Pat. Off. . |
| 20 24 195 | 11/1970 | Germany . |
| 86 00 868 | 3/1986 | Germany . |
| 39 20 706-A1 | 6/1989 | Germany . |

*Primary Examiner*—Richard J. Apley
*Assistant Examiner*—John P. Leubecker
*Attorney, Agent, or Firm*—Olson & Hierl, Ltd.

[57] ABSTRACT

A kit is provided including at least one fiber-optic bundle of the type including a plurality of flexible image fibers having an objective lens attached to one end and a connector attached to the other end. The connector is adapted to mate with a viewing device. A coating of a pressure-sensitive adhesive is also provided to secure the fiber-optic bundle to a selected one of a variety of instruments with the fiber-optic bundle conforming to the profile of that instrument over substantially the entire length with the objective lens positioned so as to include the working element of the instrument in the field-of-view. A positioning device is used to position the objective lens to ensure proper focus. The components of the kit are contained in a sterilizable enclosure which includes a bottom tray and a top cover which may be formed of a spun-bonded polyolefin fiber material.

13 Claims, 2 Drawing Sheets

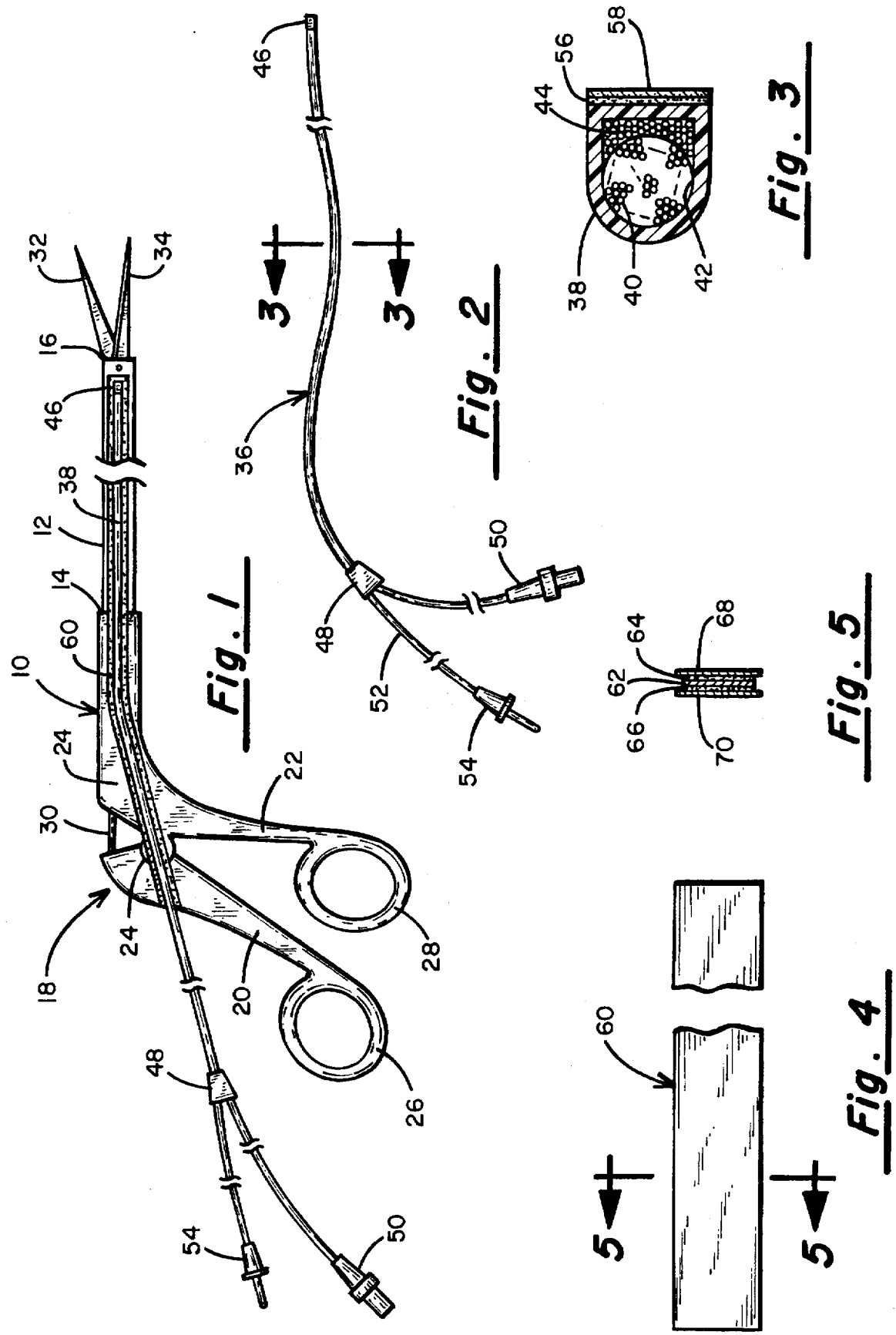

SURGICAL INSTRUMENT WITH STICK-ON FIBER-OPTIC VIEWING SYSTEM AND METHOD OF USING

BACKGROUND OF THE INVENTION

I. Field of the Invention

This invention relates generally to the field of tools, medical instruments and especially surgical instruments, and more particularly to an improvement made to conventional instruments that allows the user to have improved visibility of the interaction between the working ends of those tools or instruments and the object or tissue being worked on.

II. Discussion of the prior Art

In a co-pending application of Finn, et al., entitled SURGICAL INSTRUMENT INCORPORATING FIBER OPTIC VIEWING SYSTEMS, which is being filed concurrently herewith and whose teachings are hereby incorporated by reference, there is described a combination of a tool, such as a surgical instrument, of the type having a handle member at a proximal end thereof, a working element, such as scissors blades, forceps jaws, rongeur blades or a scalpel blade at its distal end, the two being joined together by a rigid shaft and at least one fiber-optic bundle affixed to the exterior of the instrument and extending along substantially the entire length of the handle and shaft. The objective lens of the fiber-optic bundle is accurately positioned relative to the instrument's working element so as to allow viewing of the engagement between the working element and the tissue being manipulated. By coupling the fiber-optic bundle to a suitable viewing device at its proximal end, the surgeon may observe the engagement between the working element of the instrument and the tissue being manipulated, even when that tissue is internal to the body and not directly viewable through an incision.

The invention of the aforereferenced copending application presumes that the fiber-optic bundle or bundles will be secured to the instrument as a factory operation. A need exists, however, for applying the principles of that invention to existing instruments that may already be present in a hospital's inventory. Accordingly, it is a principal object of the present invention to provide a kit, allowing a surgical assistant to append fiber-optic viewing assemblies to existing instruments immediately prior to their use.

SUMMARY OF THE INVENTION

The viewing optics kit of the present invention comprises at least one fiber-optic bundle of the type including a plurality of elongated, flexible, image fibers having first and second ends with an objective lens attached to said first end and a connector attached to the second end. The connector is adapted to mate with a viewing device. The image fibers are contained within a flexible sheath which may also contain a plurality of illumination fibers. An attachment means is also included in the kit and is adapted to secure the fiber-optic bundle(s) to the exterior surface of a selected one of a variety of instruments with the fiber-optic bundle(s) following and conforming to the profile of that instrument over substantially its entire length and with the objective lens on the fiber-optic bundle(s) positioned so as to include in the field-of-view of the lens the working element of the instrument with which it is used.

The components of this kit, prior to use, are preferably contained within an enclosure of the type including a bottom tray having compartments formed therein for retaining one or more fiber-optic bundles and the attachment means. A top cover, which may be formed from a spun-bonded polyolefin fiber material, completes the enclosure. By using this material, the kit can be sterilized after the fiber-optic bundle and the attachment means are enclosed within the enclosure.

In accordance with the invention, the attachment means may be a coating of a pressure-sensitive adhesive on the sheath of the fiber-optic bundle or strips of double-sided pressure-sensitive adhesive tape having release paper protecting the adhesive layers. The surgeon's assistant, when in the operating room, may unseal the enclosure and use the doubled-sided adhesive tape or coating to adhere the fiber-optic bundle to the exterior surface of the instrument.

As a further feature of the invention, the kit may include locating means such as a positioning device or jig adapted to fit the particular instrument and which functions to accurately fix the position of the objective lens on the distal end of the fiber-optic bundle to ensure that the lens will be properly focused so as to include at least a portion of the instrument's working element in its field-of-view.

BRIEF DESCRIPTION OF THE DRAWINGS

FIG. 1 is a side elevation of a typical surgical instrument with which the viewing optics of the present invention may be used;

FIG. 2 illustrates a fiber-optic bundle component of the kit;

FIG. 3 is a cross-sectional view of the fiber-optic bundle taken along the line 3—3 in FIG. 2;

FIG. 4 illustrates one form of an attachment means included in the kit for securing the fiber-optic bundle of FIG. 2 to the instrument;

FIG. 5 is a cross-sectional view taken along the line 5—5 in FIG. 4;

DETAILED DESCRIPTION OF THE PREFERRED EMBODIMENT

Figure 6:
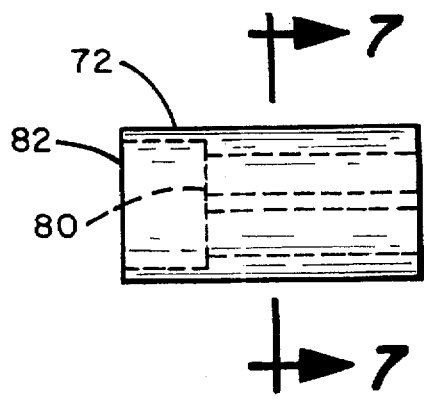
FIG. 6 is a side elevation of a positioning device useful in properly locating the distal end of the fiber-optic bundle relative to the instrument's working element.
Figure 7:
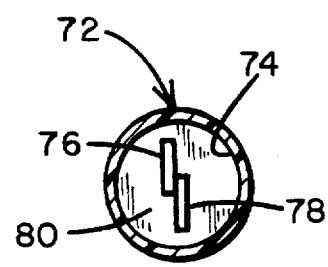
FIG. 7 is a cross-sectional view taken along the line 7—7 in FIG. 6.

An overall understanding of the novel aspects of the present invention can be gained from a consideration of the apparatus illustrated in FIG. 1. Identified generally by numeral 10 is a tool or instrument, represented as a surgical scissors, which may, for example, be used during the course of laparoscopic surgery. It includes an elongated tubular barrel or shaft 12 having a proximal end 14 and a distal end 16. Fixedly attached to the proximal end 14 is a handle member 18 which includes first and second levers 20 and 22 which are pivotally joined at a hinge point 24 and which include finger-receiving loops 26 and 28 at the lower end thereof. The lever 22 has an integrally formed barrel segment 24 having an internal bore formed therein for receiving the proximal end portion of the shaft 12.

Extending through that bore and the lumen of the tubular shaft 12 is a push-pull rod 30 whose proximal end is fixedly attached to the movable lever member 20. The other end of the push-pull rod 30 leads to the instrument's working element which, in the instrument of FIG. 1, comprises a movable scissors blade 32 which is arranged to cooperate with a fixed blade 34. By manipulating the scissors handle 18 in a conventional fashion, the motion is transmitted through the push-pull rod 30 to the movable blade 32, causing it to open and close relative to the fixed blade 34. The lumen of the tubular shaft 12 may be provided near its proximal end with a flush port, allowing saline to be ejected for clearing blood from the area of the working element.

The instrument thus far described is entirely conventional and is being used to illustrate the manner in which the viewing optics kit of the present invention may be utilized. Those skilled in the art, however, will appreciate that the invention herein described is much more versatile and can be applied to a wide variety of different surgical instruments or other types of tools. For example, by referring to the aforereferenced copending application, it can be readily appreciated that the stick-on optics can likewise be used with grasping instruments, such as forceps, and other cutting instruments, such as scalpels, hook knives, electrosurgical instruments, arthroscopic rotary cutting/debridement tools, etc.

Referring momentarily to FIG. 2, there is indicated generally by numeral 36 a fiber-optic bundle which may, for example, comprise the type of device described in the Utsumi et al. U.S. Pat. No. 4,867,529. That patent describes a super-thin fiber scope having a main scope body which is shown in cross-section in the view of FIG. 3. It comprises an outer tubular sheath 38 surrounding a large plurality of very fine image fibers 40. The image fibers are fused together at the opposed ends of the device so that they remain in relative registration. With a sheath 38 having an outside diameter of about 0.5 mm, it is currently possible to contain as many as 10,000 image fibers 40 to thereby provide excellent resolution of the image being observed. It is expected that with strides being made in fiber-optic technology, even greater numbers of fibers will be containable in a sheath of this size in the next few years.

Also shown as being contained within the outer sheath 38 is a bundle 42 of light or illumination fibers 44, which allows light to be transmitted from the proximal end of the fiber scope 36 to its distal end to thereby illuminate the scene in the field-of-view of the device. It should be recognized, however, that a separate illumination bundle can be used along with a bundle of image fibers and that they need not be within a common sheath. Moreover, there may be only a single illumination fiber. There is also affixed to the distal end of the fiber-optic bundle 36 an objective lens 46 which functions to collect the light reflected from the objects being viewed and which focuses that light on the distal ends of the image fibers.

Located near the proximal end of the bundle 36 is a hub 48 where the light fibers 44 are separated from the image fibers 40 and are brought out to a connector 50 adapted to mate with a light source (not shown). Likewise, the image fibers in the bundle 36 are brought out through a sheath 52 to a connector 54 adapted to mate with a viewing device, such as an eyepiece or a video camera. Once the image being observed is captured by the video camera, it can be processed for display on a cathode ray tube, all as is well known in the art.

Referring again to FIG. 1, it can be seen that the fiber-optic bundle 36 is affixed to the exterior surface of the instrument 10 along substantially the entire length thereof and with the objective lens 46 positioned so that at least a portion of the working element of the instrument (blades 32 and 34) fall within with the field-of-view of that lens. While only one bundle is shown attached to the instrument, it is contemplated that two or more of such bundles may be attached to provide a view from differing perspectives.

Several ways are contemplated for adhering the fiber-optic bundle 36 to the exterior surface of the instrument. As shown in FIG. 3, a coating 56 of a suitable pressure-sensitive adhesive may be applied to a predetermined surface of the outer sheath 38 of the fiber-optic bundle(s), with that adhesive layer being protected by a strip of release paper 58. Prior to the use of the instrument in a surgical procedure, a surgical assistant may remove the fiber-optic bundle 36 from its sterile pack (FIG. 8) and then peel off the release paper layer 58 as the fiber-optic bundle 36 is strung along and pressed against the surface of the instrument. Alternatively, double-sided pressure-sensitive tape strips, as at 60 in FIG. 4, may be used to effect the attachment. As shown in the cross-sectional view of FIG. 5, the tape strip 60 comprises a thin, flexible film substrate 62 which is coated on its opposed major surfaces with first and second layers 64 and 66 of pressure-sensitive adhesive. Release paper layers 68 and 70 may be used to shield the adhesive layers until the strip is to be used. The tape strips may be straight, curved, or a combination of the two so that there will be no appreciable wrinkling of the attachment means as it is affixed to the tool's surface. It is also contemplated that the instrument may have appropriate markings thereon or a groove formed therein for facilitating the routing of the tape strips and, ultimately, the fiber-optic bundle along the exterior of the instrument.

Again, referring to FIG. 1, it can be seen that one of the release paper layers 68 or 70 has been peeled back as the exposed adhesive layer is pressed against the instrument while it is being routed over the exterior surface thereof. Once that tape strip has been affixed to the instrument, the other strip of release paper may be peeled from the doubled-sided adhesive strip, allowing attachment of the fiber-optic bundle 38 to the now-exposed, adhesive on the strip. Rather than using pressure-sensitive adhesives, an instant setting glue, dispensed from a glue tube included in the kit, can be used.

To facilitate placement and accurate positioning of the objective lens 46 relative to the working element of the instrument, it has been found convenient to employ a positioning device 72 as shown in FIG. 6. It comprises a generally cylindrical member which may be molded from plastic and which includes a cavity 74 of generally cylindrical cross-section for receiving a predetermined distal portion of the shaft 12 therein. A pair of longitudinally extending slots 76 and 78 dimensioned to receive the blades 32 and 34 therein extend longitudinally from the surface 80. When the distal end of the shaft 12 is bottomed against the surface 80 and the objective lens 46 is positioned against the reference edge 82, the lens 46 will be properly distanced so as to be focused on a predetermined portion of the blades so that they fall into the field-of-view of the lens. The lens is located sufficiently close to the open distal end 16 of the shaft 12 so that if a flushing liquid, such as saline, is injected into the shaft at its proximal end, it will serve to clean the lens, should it become coated with blood or other body fluids.

Those skilled in the art will appreciate that a variety of positioning devices 72 may be included as a part of the kit to facilitate locating the objective lens of the fiber-optic bundle on a variety of surgical instruments. While positioning jigs of the type described have been found to allow rapid and accurate positioning, it is also possible to hook up the viewing device (not shown) to the connector 54 and then, while viewing the image, positioning the objective lens 46 onto the instrument when the field-of-view being observed includes a portion of the instrument's working element as well as objects lying slightly beyond the distalmost ends of the working element.

Figure 8:
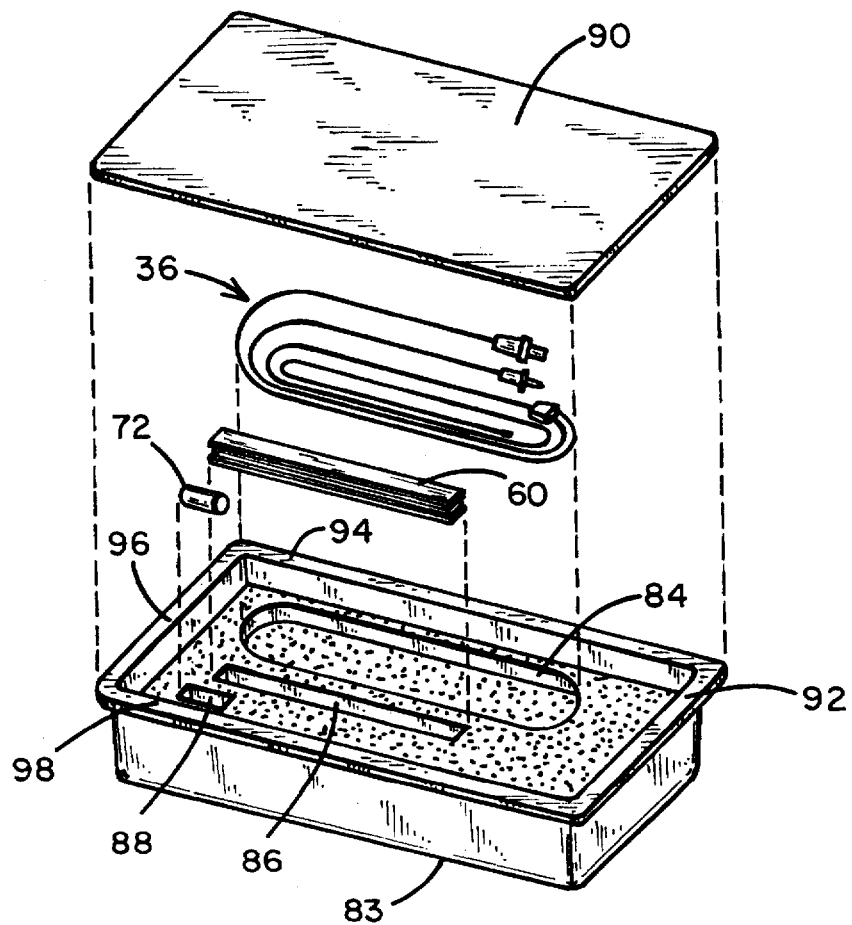
FIG. 8 illustrates the packaging system for the viewing optics kit of the present invention.

Referring next to FIG. 8, there is shown a blown-apart, perspective view of the kit elements heretofore described and an enclosure for containing those parts during shipment and storage. The enclosure includes a bottom cover or tray 83, preferably formed from plastic in a vacuum-forming operation, so as to provide cavities or compartments as at 84, 86 and 88. The cavity 84 is designed to receive the fiber-optic bundle(s) 36 therein when wrapped as a coil. The cavity 86 is designed to contain one or more double-sided adhesive strips 60. Cavity 88 receives the positioning jig 72 therein. While only one such jig is illustrated, additional cavities can be provided in the bottom cover for retaining other jigs to be used with different instruments.

With the components in place in the tray 83, a cover member 90 is appropriately sealed to the side flanges 92, 94, 96 and 98 of the tray bottom. The top cover member 90 is preferably fabricated from spun-bonded plastic fibers, such as polyolefin, such as Tyvek (a registered trademark of the Dupont Corporation). This material is preferred in that it allows the package to be sterilized after the components are sealed within the enclosure.

While the invention has been particularly shown and described with reference to a preferred embodiment, those skilled in the art will appreciate that various changes and modifications in form and detail may be made therein without departing from the scope and spirit of the invention. For example, it is not necessary that the fiber-optic bundle 36 contain the illumination fibers within the sheath 38. Instead, they may be contained in a separate sheath and routed in parallel relation to the image fibers. Moreover, the positioning devices for establishing an accurate point of attachment of the objective lens 46 to the instrument body will vary, depending upon the type of instrument to which the stick-on optic-fiber is to be applied. Accordingly, modifications, such as those suggested above, but not limited thereto, are to be considered to fall within the scope of the invention.

What is claimed is:

1. A viewing optics kit for use with any one of a variety of tools and instruments having an exterior surface, a length, a profile, and a working element, the kit comprising the combination of:
    (a) a fiber-optic bundle including a plurality of elongated, flexible image fibers having first and second ends with an objective lens attached to said first end and a connector attached to said second end for mating with a viewing device, said plurality of image fibers being contained within a flexible sheath;
    (b) a pressure-sensitive adhesive on said flexible sheath adapted to secure said fiber-optic bundle to the exterior surface of a selected one of said variety of tools and instruments with said fiber-optic bundle following and conforming to the profile of said selected one of said tools and instruments over substantially its entire length and with said objective lens positioned in viewing relation to said working element; and
    (c) an enclosure containing said fiber-optic bundles and a locating means adapted to fit said instrument for accurately fixing the position of said objective lens on said distal end of said fiber-optic bundle to ensure that said lens will be properly focused so as to include at least a portion of said instrument's working element in its field of view.

2. A viewing optics kit as in claim 1 wherein said adhesive is covered by a removable release paper prior to its removal and attachment to said selected tool/instrument in the field.

3. A viewing optics kit as in claim 1 wherein said enclosure comprises a bottom tray including raised walls for retaining said fiber-optic bundle and said locating means and a top cover formed of spun bonded polyolefin fibers, said kit being sterilized after said fiber-optic bundle and said locating means are enclosed within said enclosure.

4. A surgical kit for use with a surgical instrument of the type having an elongated shaft with a handle member at the proximal end thereof and a working element at the distal end thereof, said surgical instrument having an exterior surface, a profile, and a length, comprising:
    (a) a fiber-optic bundle including a plurality of elongated flexible image fibers having first and second ends, there being an objective lens attached to said first end and a connector attached to said second end, said connector adapted to mate with a viewing device, said plurality of image fibers being contained within a flexible sheath;
    (b) a pressure-sensitive adhesive on said flexible sheath adapted to secure said fiber-optic bundle to the exterior surface of a selected surgical instrument with said fiber-optic bundle following and conforming to the profile of said handle and shaft over substantially their entire length, with said objective lens of said fiber optic bundle positioned to view at least a part of said working element; and locating means adapted to fit said instrument for accurately fixing the position of said objective lens on said distal end of said fiber-optic bundle to ensure that said lens will be properly focused so as to include at least a portion of said instrument's working element in its field-of-view.

5. The kit as in claim 4 wherein said adhesive comprises a double-sided pressure sensitive adhesive strip.

6. The kit as in claim 5 wherein the adhesive on said double-sided, pressure-sensitive adhesive strip is protected prior to use by first and second release paper layers.

7. The kit as in claim 4 and further comprising an enclosure containing said fiber-optic bundle and said locating means.

8. The kit as in claim 7 wherein said enclosure comprises a bottom tray including raised walls for retaining said fiber-optic bundle and said locating means and a top cover formed of spun bonded polyolefin fibers, said kit being sterilized after said fiber-optic bundle and said locating means are enclosed within said enclosure.

9. The kit as in claim 4 wherein said locating means for fixing the position of said objective lens relative to said working element is a positioning device having a cross-section defining a cavity for receiving said distal portion of said elongated shaft and a surface; said positioning device defining at least one slot extending longitudinally from said surface through said positioning device for receiving said working element of said instrument.

10. The kit as in claim 9 and further including an enclosure containing said fiber-optic bundle and said locating means.

11. The kit as in claim 4 further comprising a surgical instrument having a handle and a shaft wherein at least one of said handle and shaft include a guide groove for at least partially receiving a portion of said fiber-optic bundle.

12. The kit as in claim 4 and further including at least one illumination fiber, said adhesive adapted to secure at least one illumination fiber to the exterior surface of said selected surgical instrument.

13. A method of performing a surgical procedure comprising the steps of:
    (a) surgically creating an opening leading to a surgical site;

(b) providing a surgical instrument having an elongated rigid shaft with a proximal end and a distal end, there being a working element at said distal end of said shaft for manipulating tissue, a handle element affixed to said proximal end of said shaft;

(c) providing an elongated, flexible fiber-optic assembly, said assembly including a plurality of image fibers with an objective lens at the distal end of said image fibers for defining a field-of-view;

(d) affixing said fiber-optic assembly to said rigid shaft along substantially the entire length thereof using a double-sided, pressure-sensitive adhesive strip adapted to be secured to said fiber-optic assembly such that said working element falls within said field-of-view;

(e) accurately fixing the position of said objective lens on said distal ends of said image fibers to ensure that said lens will be properly focused so as to include at least a portion of said instrument's working element in its field-of-view;

(f) connecting a proximal end of said image fibers to a viewing device; and (g) inserting said surgical instrument into said opening and advancing said working element to said surgical site while observing said viewing device.

* * * * *